United States Patent
Kim et al.

(10) Patent No.: US 11,123,385 B2
(45) Date of Patent: Sep. 21, 2021

(54) **PHARMACEUTICAL COMPOSITION AND HEALTHY FOOD COMPOSITION WITH *LACTOBACILLUS* SP. KCCM 11826P FOR PREVENTING OR TREATING HYPERPHOSPHATEMIA IN CHRONIC KIDNEY DISEASE**

(71) Applicants: KOREA FOOD RESEARCH INSTITUTE, Jeollabuk-do (KR); Catholic Kwandong University Industry Foundation, Gangneung-si (KR)

(72) Inventors: Hyo Jin Kim, Yongin-si (KR); Hae Won Jang, Seongnam-si (KR); Young-Wook Chin, Seongnam-si (KR); Woo Kyung Kang, Seoul (KR); Sung Jin Moon, Seoul (KR)

(73) Assignees: Korea Food Research Institute, Jeollabuk-do (KR); Catholic Kwandong University Industry Foundation, Gangneung-si (KR)

( * ) Notice: Subject to any disclaimer, the term of this patent is extended or adjusted under 35 U.S.C. 154(b) by 64 days.

(21) Appl. No.: 16/302,177

(22) PCT Filed: Jan. 26, 2017

(86) PCT No.: PCT/KR2017/000997
§ 371 (c)(1),
(2) Date: Nov. 16, 2018

(87) PCT Pub. No.: WO2017/200183
PCT Pub. Date: Nov. 23, 2017

(65) Prior Publication Data
US 2019/0240270 A1  Aug. 8, 2019

(30) Foreign Application Priority Data
May 17, 2016 (KR) .................. 10-2016-0059925

(51) Int. Cl.
*A61K 35/747* (2015.01)
*A23L 33/135* (2016.01)
*C12N 1/20* (2006.01)
*C12R 1/225* (2006.01)
*A61P 13/12* (2006.01)

(52) U.S. Cl.
CPC .......... *A61K 35/747* (2013.01); *A23L 33/135* (2016.08); *A61P 13/12* (2018.01); *C12N 1/205* (2021.05); *C12R 1/225* (2013.01)

(58) Field of Classification Search
CPC ....... A61K 35/747; A61P 13/12; C12R 1/225; A23L 33/135; A23V 2002/00; A23V 2250/206; A23V 2200/30; A23Y 2220/00
USPC ..................................................... 424/93.45
See application file for complete search history.

(56) References Cited

FOREIGN PATENT DOCUMENTS

| | | |
|---|---|---|
| EP | 3 459 369 A1 | 3/2019 |
| JP | 2006-176450 A | 7/2006 |
| KR | 10-2010-0126521 A | 12/2010 |
| KR | 10-1072196 B1 | 10/2011 |
| KR | 10-2012-0100608 A | 9/2012 |
| KR | 10-1355266 B1 | 2/2014 |
| KR | 10-1404285 B1 | 6/2014 |
| KR | 10-1684289 B1 | 12/2016 |
| WO | 2009/116382 A1 | 9/2009 |

OTHER PUBLICATIONS

Kuroda, A. et al., Patent Translate of JP2006176450, Jul. 6, 2006. (Year: 2006).*
Alcantara et al., "Accumulation of Polyphosphate in Lactobacillus spp. and Its Involvement in Stress Resistance", Applied and Environmental Microbiology, 2014, vol. 80, No. 5, pp. 1650-1659.

* cited by examiner

*Primary Examiner* — Louise W Humphrey
*Assistant Examiner* — Anjali Ajit Hirani
(74) *Attorney, Agent, or Firm* — Vorys, Sater, Seymour and Pease LLP; Mih Suhn Koh

(57) ABSTRACT

Provided are a functional food or pharmaceutical composition or a method for preventing, alleviating or treating hyperphosphatemia and chronic kidney disease and treating chronic kidney disease using the composition comprising *Lactobacillus* sp. KCCM 11826P having excellent phosphorus-absorbing ability.

4 Claims, 4 Drawing Sheets

PHARMACEUTICAL COMPOSITION AND HEALTHY FOOD COMPOSITION WITH *LACTOBACILLUS* SP. KCCM 11826P FOR PREVENTING OR TREATING HYPERPHOSPHATEMIA IN CHRONIC KIDNEY DISEASE

BACKGROUND OF THE INVENTION

Field of the Invention

The present invention relates to a pharmaceutical composition and a health functional food for preventing hyperphosphatemia and treating chronic kidney disease using a *Lactobacillus* sp. KCCM 11826P strain with excellent phosphorus-absorbing ability.

Description of the Related Art

The worldwide increase in the elderly population has brought about an increase in patients who suffer from adult diseases such as diabetes and hypertension. Diabetes and hypertension are the most common causes of chronic renal failure and the number of chronic renal failure patients caused by such diseases has also rapidly increased. In Korea, the onset of chronic renal failure is increasing every year. Especially, elderly people over 65 years old have a higher onset rate.

Patients with chronic renal failure have a higher mortality rate than normal people and the survival rate is also very low, specifically, 65% for men and 68% for women. Patients with chronic renal failure are known to undergo much more severe vascular calcification than normal people and vascular calcification is an important factor in cardiovascular disease.

Meanwhile, it was reported that, for hemodialysis patients, as blood phosphorus concentration increases up to the target value or more, vascular calcification and mortality increase proportional to the blood phosphorus concentration. Thus, control over blood phosphorus concentrations is important for reducing cardiovascular diseases and, furthermore, for reducing the mortality of patients with chronic renal failure.

Therefore, in order to prevent the onset of cardiovascular diseases in patients with chronic renal failure, it is necessary to further control blood calcium and phosphorus concentrations (5.5 mg/dL or less) in addition to control of drug and dietary. Most chronic kidney failure patients are recommended to eat low-phosphorus food and additionally take phosphorus binders during meals to prevent phosphorus from being absorbed into the body. However, only 40% to 50% of hemodialysis patients are reported to have reached their target blood phosphorus concentrations, which means that they have difficulty in controlling blood phosphorus concentrations.

Meanwhile, drugs for treating increased blood phosphorus concentrations are based on calcium or commercially available as replacements for calcium-based phosphorus binders. These phosphorous binders bind to phosphorus in food in the intestines and are released into the feces, thereby inhibiting the increase of blood phosphorus concentration. There among, calcium can control the concentration of phosphorus in blood, but has a disadvantage of increasing the concentration of calcium in blood. Although phosphorus binders such as sevelamer carbonate and lanthanum carbonate have been used instead of calcium, there are disadvantages such as high drug costs, low phosphorus bonding ability, potential risks due to heavy metals, and inconvenience of administration.

Accordingly, there is an urgent need for the development of pharmaceutical compositions and health functional foods for replacement of conventional calcium-based phosphorus binders.

Accordingly, as a result of extended and thorough efforts to develop materials capable of replacing conventional calcium-based phosphorous binders, the present inventors selected lactic acid bacteria having the highest phosphorus-absorbing ability among various lactic acid bacteria and completed the present invention based on this lactic acid bacteria.

SUMMARY OF THE INVENTION

Therefore, the present invention has been made in view of the above problems, and it is an object of the present invention to develop and provide a pharmaceutical composition and a health functional food for preventing or treating chronic renal diseases which exhibit complications of hyperphosphatemia by selecting strains having excellent phosphorus-absorbing ability among lactic acid bacteria beneficial to the human body and using the strains as replacements for conventional phosphorous binders.

In accordance with the present invention, the above and other objects can be accomplished by the provision of a food composition for improving hyperphosphatemia containing *Lactobacillus* sp. KCCM 11826P as an active ingredient.

In addition, regarding the food composition for improving hyperphosphatemia according to the present invention, the hyperphosphatemia is preferably caused by renal failure.

Cardiovascular disease draws a great deal of attention as one of the main causes of mortality in chronic renal failure patents. If the kidney fails to function to excrete phosphorus due to kidney disease, the blood phosphorus concentration is increased, and the increased phosphorus binds to calcium to form calcium-phosphorus bonds. The calcium-phosphorus bonds thus formed are deposited in heart valves, aorta, coronary arteries and the like, which causes cardiovascular disease and death. Currently, in order to prevent such vascular calcification, patients take phosphorus binders. However, because conventional phosphorus binders are based on calcium, they decrease phosphorus concentrations and at the same time, increase calcium concentrations. Due to this, phosphorus and calcium bind to each other to form calcium-phosphorus bonds, which causes not only vascular calcification, but also side effects including hypercalcemia and gastrointestinal disorders such as abdominal distension.

The present inventors screened *Lactobacillus* sp. KCCM 11826P as lactic acid bacteria with excellent phosphorus-absorbing ability, thereby developing technologies capable of solving disadvantages of calcium-based phosphorus binders and effectively controlling phosphorus concentrations.

In addition, regarding the food composition for improving hyperphosphatemia according to the present invention, the food composition is preferably any one selected from patient nutritional meals, meats, cereals, caffeinated beverages, regular beverages, dairy products, chocolate, bread, snacks, confectionery, pizza, jelly, noodles, gums, ice cream, alcoholic beverages, liquor, vitamin complexes and other health supplement foods. When the food composition is prepared into the form described above, it can be easily and conveniently administered to patients who suffer from diseases caused by increased blood-phosphorus concentrations.

Lactic acid bacteria have been used in a variety of forms such as food, for example, yogurt, lactic acid bacteria fermented milk or the like, which are easily digested and *Lactobacillus*, which is one of lactic acid bacteria, is lactic acid bacteria that plays a key role in the fermentation of Korean traditional foods such as Kimchi and is known to help strengthen the human immune system. Accordingly, lactic acid bacteria selected by the present invention, i.e., *Lactobacillus* sp. KCCM 11826P, exhibit excellent phosphorus-absorbing ability and is beneficial to the human body and useful for various food groups, and is thus suitable as a health food composition for improving hyperphosphatemia.

Meanwhile, the present invention provides a pharmaceutical composition for preventing or treating hyperphosphatemia containing *Lactobacillus* sp. KCCM 11826P as an active ingredient.

The *Lactobacillus* sp. KCCM 11826P selected by the present invention is not based on calcium, unlike these conventional phosphorus binders, so that it does not cause diseases associated with hyperphosphatemia and is suitable for mass-production and thus can be used at very low cost.

In addition, regarding the pharmaceutical composition for preventing hyperphosphatemia and treating chronic kidney diseases according to the present invention, the hyperphosphatemia is preferably caused by renal failure.

In addition, regarding the pharmaceutical composition for preventing hyperphosphatemia and treating chronic kidney diseases according to the present invention, the pharmaceutical composition is preferably any one selected from granules, lemonades, powders, syrups, liquids and solutions, extracts, elixirs, fluid extracts, suspensions, decoctions, infusions, tablets, spirits, capsules, troches, pills, and soft and hard gelatin capsules. The pharmaceutical composition prepared into the formulation described above enables the present ingredients to be delivered to the human body and is easy to administer.

Meanwhile, the dose of the pharmaceutical composition for preventing hyperphosphatemia and treating chronic kidney diseases according to the present invention is preferably determined depending on administration method, age, gender and body weight of a taker, severity of disease and the like. For example, the pharmaceutical composition for preventing hyperphosphatemia and treating chronic kidney diseases according to the present invention can be administered one or more times at a daily dose of 0.00001 to 100 mg/kg (body weight). However, the dose is provided as an example for illustration and can be changed by the physician's prescription depending on conditions of the taker.

Advantageous Effects

According to the present invention, *Lactobacillus* sp. KCCM 11826P selected by the present invention exhibits excellent phosphorus-absorbing ability and thus can exhibit phosphorus absorption into the human body in the intestines. That is, when *Lactobacillus* sp. KCCM 11826P according to the present invention is administered, phosphorus present in food can be absorbed in the intestines and is released into the feces, thereby effectively controlling the phosphorus concentration.

In addition, the present invention can replace conventional calcium-based phosphorus binders, so that side effects caused by increased blood calcium concentrations can be minimized, and kidney disease complications associated with hyperphosphatemia can be effectively prevented or treated.

In addition, the *Lactobacillus* sp. KCCM 11826P selected by the present invention can be administered at a low price as compared to conventional phosphorus binders, can be developed into yogurt, powders, patient nutritional meals and the like, based on characteristics of strains, and can be thus administered more easily than conventional phosphorus binders.

In addition, the lactic acid bacteria of the present invention, i.e., *Lactobacillus* sp. KCCM 11826P, can stay in the intestines for a long time, can be administered at a longer interval than conventional phosphorus binders and can effectively control the concentration of phosphorus in the intestines.

BRIEF DESCRIPTION OF THE DRAWINGS

The above and other objects, features and other advantages of the present invention will be more clearly understood from the following detailed description taken in conjunction with the accompanying drawings, in which:

FIG. 1A is an image showing that colonies turn blue green by a reagent since strains absorb phosphorus, and FIG. 1B is an image showing that colonies do not turn blue green by a reagent since the strains do not absorb phosphorus;

FIG. 3A is a graph showing growth rates of *Lactobacillus* sp. KCCM 11826P and *Escherichia coli* top10 strain, and FIG. 3B is a phosphorus-absorbing data of *Lactobacillus* sp. KCCM 11826P and *Escherichia coli* top10 strain.

DETAILED DESCRIPTION OF THE INVENTION

Hereinafter, the present invention will be described in more detail with reference to the following Example. The scope of the present invention is not limited to the following Example and includes modifications of technical concept equivalent thereto.

EXAMPLE 1: SCREENING OF STRAINS WITH EXCELLENT PHOSPHORUS-ABSORBING ABILITY (1) Isolation of Strains with Excellent Phosphorus-Absorbing Ability from Traditional Fermented Food In the present Example, strains with excellent phosphorus-absorbing ability were isolated from Korean traditional fermented foods such as soybean paste (called "Doenjang"), red pepper paste (called "Gochujang"), soy sauce, seasoned fish, leaven (called "Nuruk"), and Sikhae.

Traditional fermented food was dissolved in phosphate buffered saline (PBS), plated on solid TSA, MRS and LB culture media and cultured in a cell incubator under aerobic or anaerobic conditions at 30 to 37° C. for 12 to 36 hours. After culture, the phosphorus-absorbing ability of the produced colonies was evaluated by colorimetry using 5-bromo-4-chloro-3-indolyl phosphate disodium salt (Sigma).

Figure 1B:
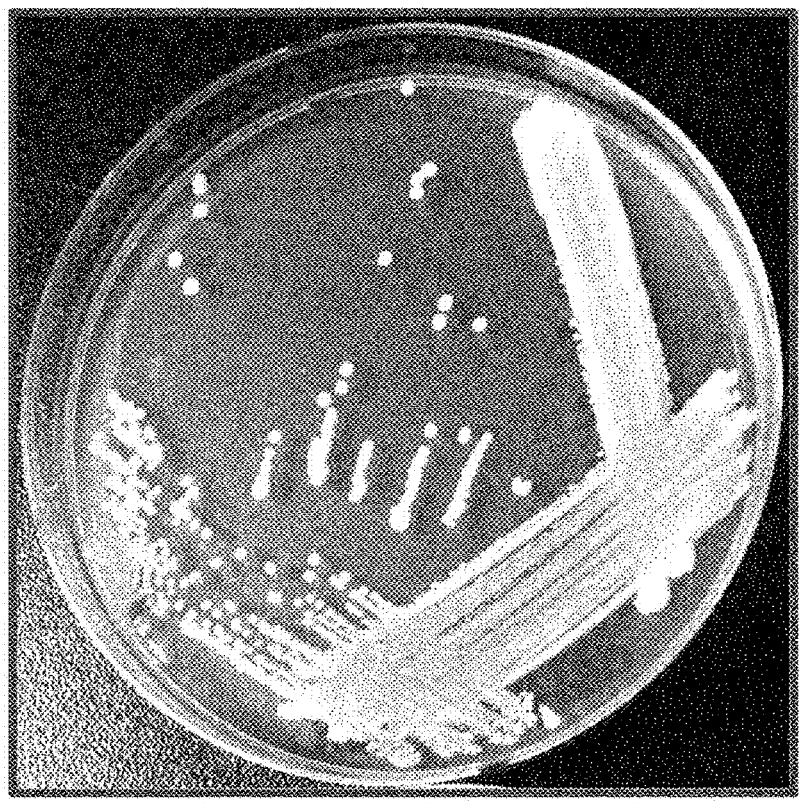
FIGS. 1A and 1B show test results through colorimetry using a 5-bromo-4-chloro-3-indolyl phosphate disodium salt reagent in order to screen strains absorbing phosphorus.
Figure 1A:
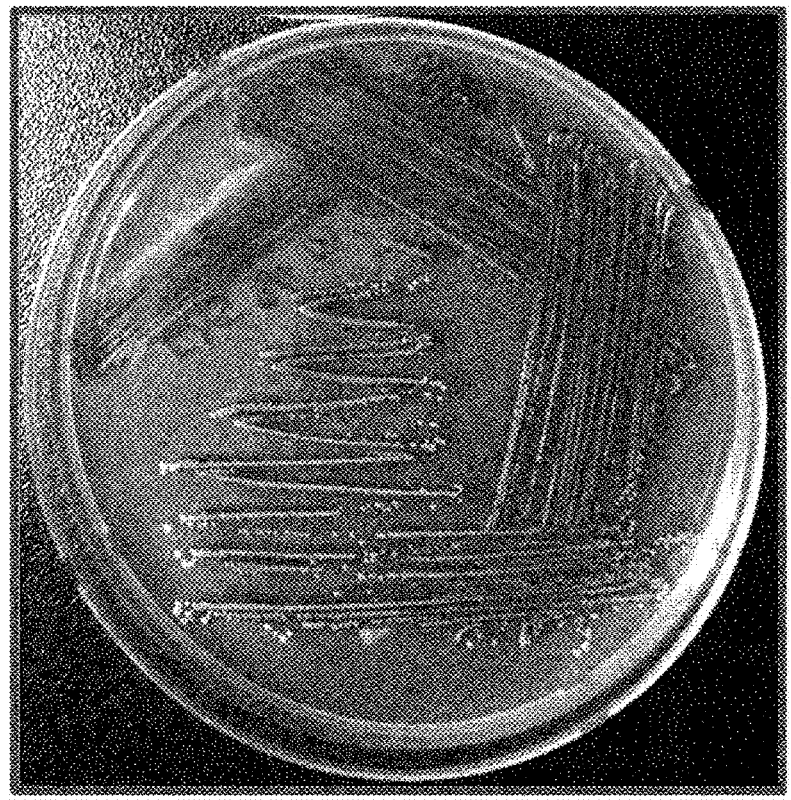

Test results showed that strains absorbing phosphorus are blue green (FIGS. 1A and 1B). FIGS. 1A and 1B show results of colorimetry tests using a 5-bromo-4-chloro-3-indolyl phosphate disodium salt reagent in order to screen strains absorbing phosphorus. FIG. 1A is an image showing that colonies turn blue green by a reagent since strains absorb phosphorus and FIG. 1B is an image showing that colonies do not turn blue green by a reagent since strains do not absorb phosphorus.

Three or more colonies with high color intensity were screened by colorimetry in a petri dish, on which strains were cultured, and these colonies were picked in a 96-well microplate MRS liquid medium for cell culture such that the total phosphorus concentration reached 20 mM and cultured in a cell incubator at 37° C. and 30° C. for 3 hours. Then, the phosphorus concentration was measured using a phosphate assay kit (Sigma).

As a result of measurement, about 150 types of strains with a great phosphorus decrease were identified in phosphorus-containing MRS liquid culture medium and primarily screened. The about 150 screened strains were pre-cultured in a shaking incubator at 37° C. and 30° C. for 6 to 36 hours at 230 rpm. Then, the numbers of cells for 150 types of strains were normalized at an optical density (OD) of 1 and main-cultured at 230 rpm in a shaking incubator in MRS liquid culture medium prepared to have the total phosphorus concentration of 20 mM at 37° C. and 30° C. for 3 hours. The difference between a phosphorus concentration 0 hours after culture and a phosphorus concentration at 3 hours after culture was calculated, divided by OD at 3 hours after culture and normalized to obtain a phosphorus absorption rate for each strain. The phosphorus absorption rate for each normalized strain is as follows:

$$P_{concentration} \text{ (phosphorus absorption rate for each strain strain)} = (P_{0h} - P_{3h})/OD_{3h} \quad \text{[Equation 1]}$$

The phosphorus absorption rate for each strain obtained by Equation 1 was comparatively analyzed and, based on the analysis results, the strain having the highest phosphorus absorption rate was screened and this strain was subjected to 16S rRNA sequence analysis. Analysis results showed that the strain has homology with Lactobacillus sp. strain, and such a screened Lactobacillus sp. strain is referred to as "Lactobacillus sp. KCCM 11826P strain", which is used in the following Test Examples 1 to 3.

Test Example 1: Identification of
Phosphorus-Absorbing Ability of Screened
Lactobacillus Sp. KCCM 11826P Strain In the present Test Example, in order to identify the phosphorus-absorbing ability of the screened Lactobacillus sp. KCCM 11826P strain, the screened Lactobacillus sp. KCCM 11826P strain was compared with generally used lactic acid bacteria in terms of phosphorus-absorbing ability.

The lactic acid bacteria used for Comparative Test were six types of genus Lactobacillus lactic acid bacteria (L. brevis JCM 1059, L. casei IAM 1045, L. acidophilus ATCC 11506, L. plantarum ATCC 10012, L. delbrueckii ATCC 7830, L. subsp. lactis ATCC 21053), two types of genus Enterococcus lactic acid bacteria (Enterococcus faecium ATCC 6057, E. faecalis IFO 3971) and one type of genus Bifidobacterium lactic acid bacteria (Bifidobacterium longum ATCC 15707).

Respective strains were cultured under optical conditions, i.e., the same conditions as pre-culture and main-culture conditions in Example 1 in MRS liquid medium having a phosphorus concentration of 20 mM. Then, phosphorus absorption rates of respective strains were obtained in accordance with Equation of the phosphorus absorption rate of Example 1 and then compared.

Figure 2:
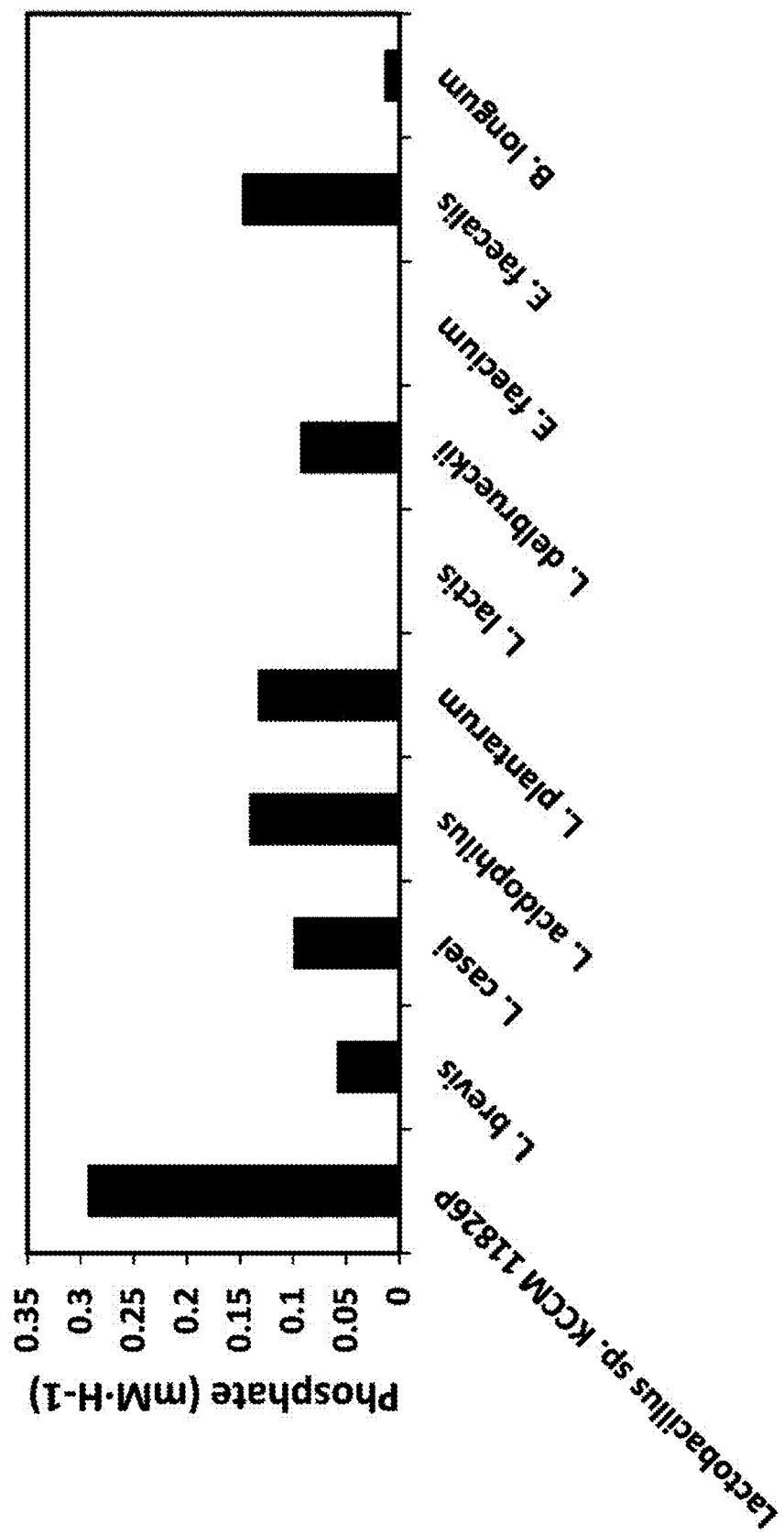
FIG. 2 shows results of comparative measurement in phosphorus-absorbing ability between the screened *Lactobacillus* sp. KCCM 11826P, six types of genus *Lactobacillus* lactic acid bacteria (*L. brevis* JCM 1059, *L. casei* IAM 1045, *L. acidophilus* ATCC 11506, *L. plantarum* ATCC 10012, *L. delbrueckii* ATCC 7830, *L.* subsp. *lactis* ATCC 21053), two types of genus *Enterococcus* lactic acid bacteria (*Enterococcus faecium* ATCC 6057, *E. faecalis* IFO 3971) and one type of genus *Bifidobacterium* lactic acid bacteria (*Bifidobacterium longum* ATCC 15707)

Test results showed that the Lactobacillus sp. KCCM 11826P strain according to the present invention screened in Example 1 exhibited the best phosphorus-absorbing ability and absorbs 0.2923 mM of phosphorus per hour at OD1, which is higher than the phosphorus-absorption amount (i.e., 0.1467 mM) of E. faecalis IFO 3971 having the best phosphorus-absorbing ability among compared strains (FIG. 2). FIG. 2 shows results of comparative measurement in phosphorus-absorbing ability between the screened Lactobacillus sp. KCCM 11826P, six types of genus Lactobacillus lactic acid bacteria (L. brevis JCM 1059, L. casei IAM 1045, L. acidophilus ATCC 11506, L. plantarum ATCC 10012, L. delbrueckii ATCC 7830, L. subsp. lactis ATCC 21053), two types of genus Enterococcus lactic acid bacteria (Enterococcus faecium ATCC 6057, E. faecalis IFO 3971) and one type of genus Bifidobacterium lactic acid bacteria (Bifidobacterium longum ATCC 15707).

Accordingly, it can be seen that the strain screened in Example 1 of the present invention, Lactobacillus sp. KCCM 11826P, exhibits excellent phosphorus absorption ability.

Test Example 2: Comparison in
Phosphorus-Absorbing Ability between Escherichia
coli Top10 and Lactobacillus Sp. KCCM 11826P The purpose of the present invention is to inhibit absorption of phosphorus in the intestines via lactic acid bacteria. Accordingly, in the present Test Example, the phosphorus-absorbing ability between the representative intestinal bacteria, i.e., Escherichia coli top10, and the Lactobacillus sp. KCCM 11826P screened by the present Example, Lactobacillus sp. KCCM 11826P, was compared to identify whether or not these bacteria are lactic acid bacteria suited to function to inhibit absorption of phosphorus in the intestines.

In order to compare the phosphorus-absorbing ability between Lactobacillus sp. KCCM 11826P and Escherichia coli top10 strain, two strains were fermented in MRS liquid medium containing 20 mM of phosphorus.

Test results showed that the Lactobacillus sp. KCCM 11826P strain had an increase in OD to 13.35 after 8 hours of fermentation, while the Escherichia coli top10 had an increase in OD to 6.65 after 8 hours of fermentation (FIG. 3A).

In addition, Lactobacillus sp. KCCM 11826P absorbed 3.17 mM of phosphorus after 8 hours of fermentation, while the Escherichia coli top10 had an increase in OD to 0.56 mM after 8 hours of fermentation.

Accordingly, the Lactobacillus sp. KCCM 11826P screened by the present invention exhibits excellent growth rate and phosphorus-absorbing ability, as compared to conventional intestinal bacteria, *Escherichia coli* top10 (FIG. 3B).

Figure 3A:
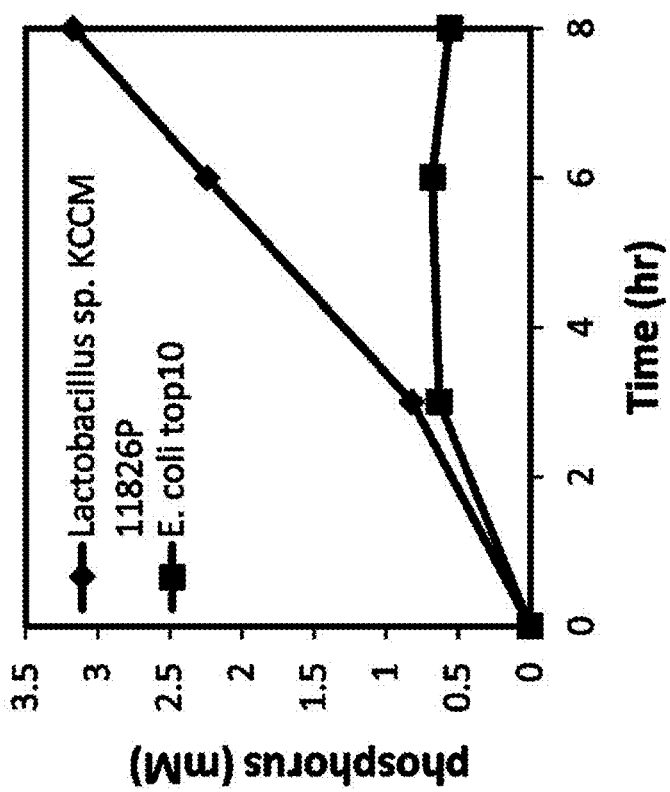
FIGS. 3A and 3B show results of comparative measurement in phosphorus-absorbing ability between *Lactobacillus* sp. KCCM 11826P and *Escherichia coli* top10 strain.
Figure 3B:
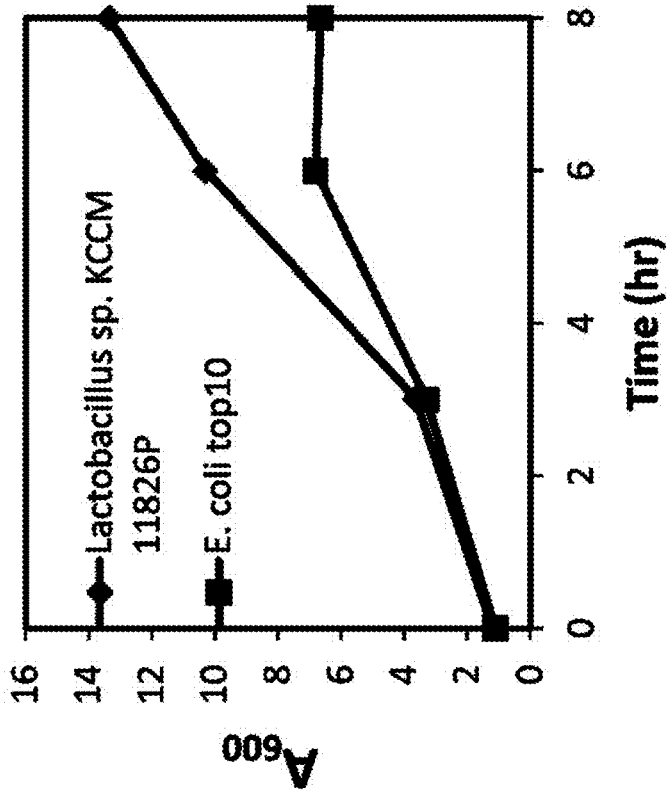

FIGS. 3A and 3B show results of comparative measurement in phosphorus-absorbing ability between *Lactobacillus* sp. KCCM 11826P and *Escherichia coli* top10 strain. FIG. 3A is a graph showing growth rates of *Lactobacillus* sp. KCCM 11826P and *Escherichia coli* top10 strain, and FIG. 3B is a phosphorus-absorbing data of *Lactobacillus* sp. KCCM 11826P and *Escherichia coli* top10 strain.

In addition, it can be seen that the *Escherichia coli* top10 strain discharges the absorbed phosphorus out of cells after 6 hours and discharges all the absorbed phosphorus out of cells after 24 hours.

Accordingly, the *Lactobacillus* sp. KCCM 11826P screened by the present invention is suitable as bacteria to inhibit absorption of phosphorous in the intestines.

Test Example 3: Comparison in Phosphorus-Absorbing Ability between *Lactobacillus* Sp. KCCM 11826P and Calcium Carbonate as Phosphorus Binder In the present Test Example, the phosphorus-absorbing ability of the calcium carbonate, which is one of phosphorus binders generally used to prevent absorption of phosphorus in the body, was compared with the phosphorus-absorbing ability of the *Lactobacillus* sp. KCCM 11826P screened by the present invention.

For comparative tests, the following Example 2, and Comparative Examples 1 and 2 were prepared.

(1) Production of Example 2

1 g/L dry weight of *Lactobacillus* sp. KCCM 11826P strain was added to 5 ml of MRS liquid medium prepared such that the phosphorus concentration reached 20 mM to prepare Example 2.

(2) Production of Comparative Example 1

Calcium carbonate was dissolved in distilled water to prepare a solution such that the concentration of calcium carbonate was 1 g/L, and the solution was added to 5 ml of MRS liquid medium prepared such that the phosphorus concentration was 20 mM, to produce Comparative Example 1.

(3) Production of Comparative Example 2

A calcium carbonate powder was added to the MRS liquid medium prepared to have the phosphorus concentration of 20 mM such that the concentration reached 1 g/L, followed by strongly stirring for 10 seconds, to produce Comparative Example 2.

Example 2, and Comparative Examples 1 and 2 were reacted in a cell incubator at 37° C. and 230 rpm for 3 hours.

Figure 4:
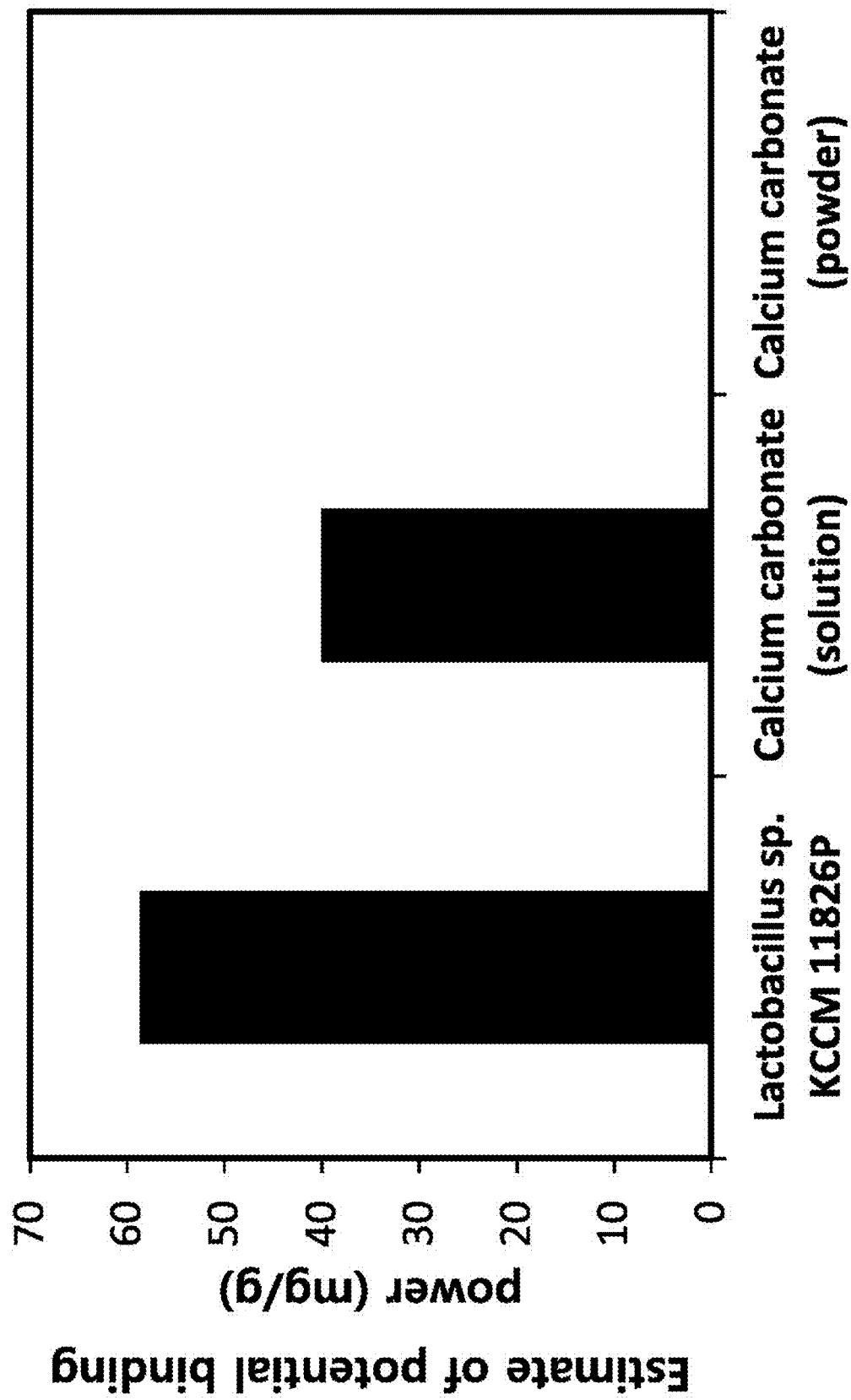
FIG. 4 shows results of comparative measurement in phosphorus absorption and adsorption ability between *Lactobacillus* sp. KCCM 11826P strain, the calcium carbonate solution and the calcium carbonate powder.

Rest results showed that, in Comparative Example 1, about 40.08 mg of phosphorus per 1 g was adsorbed and, in Comparative Example 2, phosphorus was almost not adsorbed. On the other hand, the *Lactobacillus* sp. KCCM 11826P screened by the present invention adsorbed 58.69 mg of phosphorus per 1 g, which means that the *Lactobacillus* sp. KCCM 11826P has excellent phosphorus-absorbing ability, as compared to calcium carbonate (FIG. 4). FIG. 4 shows results of comparative measurement in phosphorus absorption and adsorption abilities between *Lactobacillus* sp. KCCM 11826P strain, the calcium carbonate solution, and the calcium carbonate powder.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

ACCESSION NUMBER

Name of the depository institution: Korea Culture Center of Microorganisms (Foreign)
Accession number: KCCM11826P
Date of deposit: 20160325

| Applicant or Agent File Reference No.: YP-16-062 | International Application No. |

Indication contents to deposited microorganism or other biological material (Issued pursuant to Rule 13bis of Patent Cooperation Treaty)

The following indication items relate to deposited microorganism or other biological material losed in 15 line, page 2 in the Description of the Invention.

B. Identification of deposited material   Additional deposited material is described in the next separate page ☐

| Name of the depository institution |
|---|
| Korea Research Institute of Bioscience and Biotechnology (KRIBB) |

| Address of the depository institution (including Postal code number and National name) |
|---|
| 45 Hongjenae 2ga-gil, Hongje-dong, Seodaemun-gu, Seoul, 120-861, Republic of Korea |

| Date of deposit<br>March 25, 2015    Accession number | Accession number<br>KCCM 11826P |
|---|---|

C. Additional indication item
(leave blank unless there is stated matter) Separate additional page will be continued ☐

D. Designated States designated by indication matter (unless indication matter is available for all designated States)

E. Separate submission of indication matter (leave blank unless there is stated matter)

The following indication matter will be submitted to the International Bureau later
(Specify general feature of indication matter )

| ☐ this paper is filed together with the International application: |
|---|
| Officer |

Form PCT/RO/134 (July 1998; reprint January 2004)

What is claimed is:

1. A method of improving hyperphosphatemia or treating a chronic kidney disease in a subject in need thereof, comprising administering to the subject a composition comprising an effective amount of *Lactobacillus* sp. KCCM 11826P.

2. The method of claim 1, wherein the hyperphosphatemia is caused by renal failure.

3. The method of claim 1, wherein the composition is a food composition selected from the group consisting of patient nutritional meals, meats, cereals, caffeinated beverages, regular beverages, dairy products, chocolate, bread, snacks, confectionery, pizza, jelly, noodles, gums, ice cream, alcoholic beverages, liquor, vitamin complexes and other health supplement foods.

4. The method of claim 1, wherein the composition is a pharmaceutical composition selected from the group consisting of granules, lemonades, powders, syrups, liquids and solutions, extracts, elixirs, fluid extracts, suspensions, decoctions, infusions, tablets, spirits, capsules, troches, pills, and soft and hard gelatin capsules.

* * * * *